United States Patent
Knuuttila et al.

(10) Patent No.: US 9,382,483 B2
(45) Date of Patent: Jul. 5, 2016

(54) PROCESS AND APPARATUS FOR PRODUCING HYDROCARBONS FROM FEED-STOCKS COMPRISING TALL OIL AND TERPENE-COMPOUNDS

(75) Inventors: Pekka Knuuttila, Porvoo (FI); Jaakko Nousiainen, Lappeenranta (FI); Arto Rissanen, Lappeenranta (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 13/699,542

(22) PCT Filed: May 23, 2011

(86) PCT No.: PCT/FI2011/050462
§ 371 (c)(1),
(2), (4) Date: Nov. 21, 2012

(87) PCT Pub. No.: WO2011/148046
PCT Pub. Date: Dec. 1, 2011

(65) Prior Publication Data
US 2013/0072730 A1    Mar. 21, 2013

(30) Foreign Application Priority Data
May 25, 2010    (FI) ..................................... 20105583

(51) Int. Cl.
*C10G 3/00* (2006.01)
*C10G 45/02* (2006.01)
(Continued)

(52) U.S. Cl.
CPC  *C10G 3/50* (2013.01); *B01D 17/00* (2013.01); *B01J 8/00* (2013.01); *C07C 5/226* (2013.01);
(Continued)

(58) Field of Classification Search
CPC .............. C10G 1/06; C10G 3/00; C10G 3/50; C10L 1/04; C10L 1/16; B01J 23/84; B01J 23/883; B01J 21/04; B01J 21/08; B01J 29/00
USPC ..................... 585/16, 240, 242, 253
See application file for complete search history.

(56) References Cited

U.S. PATENT DOCUMENTS 3,312,750 A * 4/1967 Berg ....................... C07C 7/163
                                                           208/216 R
3,370,099 A     2/1968 Plank et al.
(Continued)

FOREIGN PATENT DOCUMENTS

EA     200800242 A1    6/2008
EP     1 396 531 A2    3/2004
(Continued)

OTHER PUBLICATIONS

Eick, G., Tall Oil and Terpene Derivatives, Journal of Chemical Education, vol. 34, No. 12, Dec. 1957.*
(Continued)

*Primary Examiner* — In Suk Bullock
*Assistant Examiner* — Philip Louie
(74) *Attorney, Agent, or Firm* — Birch, Stewart, Kolasch & Birch, LLP

(57) ABSTRACT

The invention relates to a process for producing hydrocarbon components, comprising: providing a feedstock comprising tall oil and terpene-based compounds; subjecting the feedstock and a hydrogen gas feed to a hydroprocessing treatment in the presence of a hydroprocessing catalyst to produce hydrocarbon components including n-paraffins, and subjecting the hydrocarbon components including n-paraffins to isomerisation in the presence of a dewaxing catalyst to form a mixture of hydrocarbon components. The invention also relates to an apparatus for implementing the process. The invention further relates to a use of the hydrocarbon components produced by the process as a fuel or as an additive in fuel compositions. The invention also relates to a use of a NiW catalyst on a support selected from $Al_2O_3$, zeolite, zeolite-$Al_2O_3$, and $Al_2O_3$—$SiO_2$ for producing fuel or an additive for fuel compositions from a feedstock comprising tall oil and terpene-based compounds.

5 Claims, 2 Drawing Sheets

(51) Int. Cl.
| | |
|---|---|
| C10G 45/06 | (2006.01) |
| C10G 45/08 | (2006.01) |
| C10G 45/12 | (2006.01) |
| C10G 45/58 | (2006.01) |
| C10G 45/60 | (2006.01) |
| C10G 45/64 | (2006.01) |
| C10G 65/04 | (2006.01) |
| C10L 1/04 | (2006.01) |
| C10L 1/06 | (2006.01) |
| C10L 1/08 | (2006.01) |
| B01D 17/00 | (2006.01) |
| B01J 8/00 | (2006.01) |
| C07C 5/22 | (2006.01) |

(52) U.S. Cl.
CPC .. *C10G 3/46* (2013.01); *C10G 3/48* (2013.01); *C10G 3/49* (2013.01); *C10G 45/02* (2013.01); *C10G 45/06* (2013.01); *C10G 45/08* (2013.01); *C10G 45/12* (2013.01); *C10G 45/58* (2013.01); *C10G 45/60* (2013.01); *C10G 45/64* (2013.01); *C10G 65/043* (2013.01); *C10L 1/04* (2013.01); *C10L 1/06* (2013.01); *C10L 1/08* (2013.01); C10G 2300/1014 (2013.01); C10G 2300/4018 (2013.01); C10G 2400/02 (2013.01); C10G 2400/04 (2013.01); C10G 2400/06 (2013.01); C10G 2400/08 (2013.01); Y02P 30/20 (2015.11)

(56) References Cited

U.S. PATENT DOCUMENTS

| | | | | |
|---|---|---|---|---|
| 5,705,722 A * | 1/1998 | Monnier | ............... | C07C 1/00 585/240 |
| 2003/0150778 A1 | 8/2003 | Haluska et al. | | |
| 2008/0308457 A1 | 12/2008 | Dindi et al. | | |
| 2009/0158637 A1 | 6/2009 | McCall et al. | | |
| 2009/0218061 A1 | 9/2009 | Schinski et al. | | |
| 2009/0229173 A1 * | 9/2009 | Gosling | ............... | 44/308 |
| 2010/0076236 A1 * | 3/2010 | Van Heuzen et al. | ............... | 585/313 |
| 2011/0049012 A1 * | 3/2011 | Stigsson | ............... | C10L 1/026 208/88 |
| 2011/0056869 A1 * | 3/2011 | Novak et al. | ............... | 208/49 |

FOREIGN PATENT DOCUMENTS

| | | |
|---|---|---|
| EP | 1 741 767 A1 | 1/2007 |
| EP | 1 956 070 A1 | 8/2008 |
| RU | 2348677 C2 | 3/2009 |
| WO | WO 99/10450 A1 | 3/1999 |
| WO | WO 2004/022674 A1 | 3/2004 |
| WO | 2007/003709 A1 | 1/2007 |
| WO | WO 2008/027699 A2 | 3/2008 |
| WO | WO 2008/058664 A1 | 5/2008 |
| WO | WO 2008/101945 A1 | 8/2008 |
| WO | 2008/152199 A1 | 12/2008 |
| WO | WO 2010/097519 A2 | 9/2010 |
| WO | WO 2011/004065 A2 | 1/2011 |

OTHER PUBLICATIONS

Casbas et al . "Catalytic Hydrodesulphurization of Terpenes." Applied Catalysis (1989), vol. 50, pp. 87-97.
International Search Report issued Nov. 7, 2011, in PCT International Application No. PCT/FI2011/050462.
Search Report issued Feb. 10, 2011, in Finnish Patent Application No. 20105583.
Written Opinion of the International Searching Authority issued Nov. 25, 2012, in PCT International Application No. PCT/FI2011/050462.
Chinese Office Action dated Mar. 11, 2014 for corresponding Chinese Application No. 201180030600.7 with English translation.
Russian Decision on Grant for Russian Application No. 2012156272/04, mailed Jun. 8, 2015, with an English translation.
Office Action dated Feb. 16, 2015 for Russian Patent Application No. 2012156272.

* cited by examiner

US 9,382,483 B2

PROCESS AND APPARATUS FOR PRODUCING HYDROCARBONS FROM FEED-STOCKS COMPRISING TALL OIL AND TERPENE-COMPOUNDS

FIELD OF THE INVENTION

The present invention relates to a process and apparatus for producing hydrocarbons. More particularly, the invention relates to a conversion of materials of biological origin to various fuel grade components useful as fuel as such, or as fuel blending components.

BACKGROUND OF THE INVENTION

Raw materials of natural origin are potential sources of various fuels or fuel components. For example, tall oil, a by-product of the kraft pulping of coniferous trees, has been widely used as raw material for hydrocarbon fuel components. There are lots of reports disclosing the production of hydrocarbons of various oils derived from renewable sources. For example, WO 2008/058664 A1, EP 1396531 A2, EP 1741767, and U.S. 2009/0158637 A1 disclose a process for producing hydrocarbon fractions by successive hydrodeoxygenation and hydroisomerisation steps of tall oil containing fatty acids and esters thereof under catalytic conditions. The hydrocarbon fractions are reported to be suitable as diesel fuels or aviation fuels.

BRIEF DESCRIPTION OF THE INVENTION

It is an object of the present invention to provide a simple and efficient process and apparatus for producing hydrocarbon components from biological feedstock comprising tall oil and terpene-based compounds in a catalytic process to various fuel grade hydrocarbon components. The objects of the invention are achieved by what is stated in the independent claims.

The process of the invention produces hydrocarbon product streams having distillation curves conforming to those of standardized diesel, gasoline, jet and naphtha fuels. As a general, hydrocarbons distilling at a temperate range from 160° C. to 370° C. are obtained as a middle distillate conforming to diesel fuel quality standard EN 590. Hydrocarbons distilling at temperatures ranging from 40° C. to 210° C. are useful as high quality gasoline fuel. They conform to standard EN 228. Hydrocarbons having a distillation temperature above 160° C. to 300° C. have potential as aviation applications, generally referred to as jet. The jet fuel conforms to standard ASTM D-1655.

It is another object of the invention to provide a use of the hydrocarbon components produced by the process of the invention as fuel or as an additive in fuel compositions.

It is a further object of the invention to provide a use of a NiW catalyst on a support selected from $Al_2O_3$, zeolite, zeolite-$Al_2O_3$, and $Al_2O_3$—$SiO_2$ for producing fuel or an additive for fuel compositions from a feedstock comprising tall oil and terpene-based compounds.

It is an advantage of the method and apparatus of the invention that raw materials of various types, differing in chemical functionalities, received from biological sources can be included in the feedstock and converted in good yields to hydrocarbon components which are useful as fuels or fuel blending components in a single process and apparatus. In a specific embodiment, the feedstock comprises crude tall oil and crude sulphate turpentine obtained as by-products from kraft pulping process of coniferous trees.

The invention provides a simple, efficient and economical process which is controllable in an improved manner producing various fuel components with good yield and quality. In a specific embodiment, the invention provides an efficient and economical process for the treatment of by-products from forest industry.

DETAILED DESCRIPTION OF THE INVENTION

Figure 1:
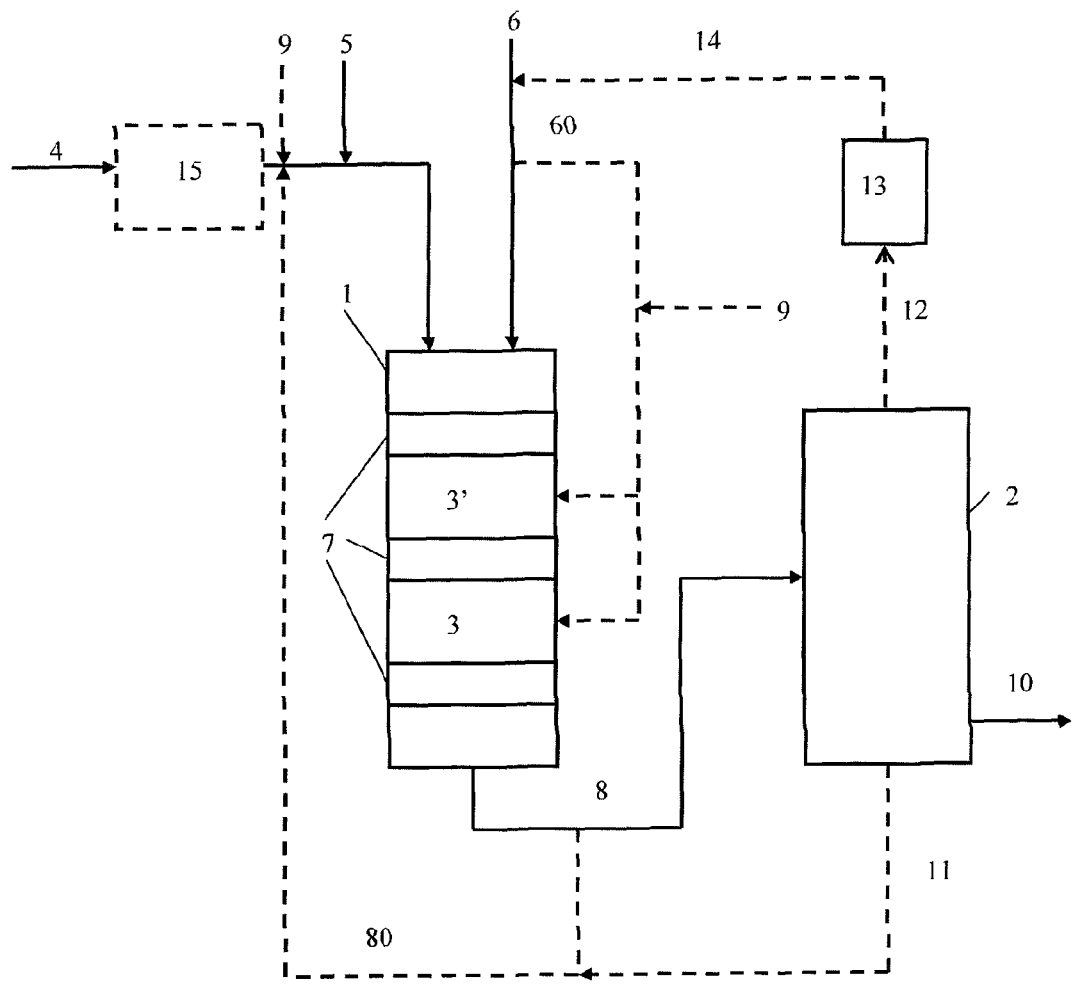
FIG. 1 shows schematically an embodiment of the apparatus of the invention.

An object of the invention is to provide a process for producing hydrocarbon components, comprising:
providing a feedstock comprising tall oil and terpene-based compounds;
subjecting the feedstock and a hydrogen gas feed to a hydroprocessing treatment in the presence of a hydroprocessing catalyst to produce hydrocarbon components including n-paraffins, and
subjecting the hydrocarbon components including n-paraffins to isomerization in the presence of a dewaxing catalyst to form a mixture of hydrocarbon components.

The terpene-based compounds can be obtained from any suitable source. In an embodiment of the invention, the terpene-based compounds are obtained from plants, terpene oils, distillation bottoms from terpene distillation and flavorants and/or fragrance industry. The terpene-based compounds are typically composed of $C_{10}H_{16}$ terpenes.

In an embodiment, the terpene-based compounds are obtained as by-products from forest industry. Terpene-based compounds from this origin are typically received as a product called crude turpentine. The crude turpentine is obtained for example from kraft pulping process of coniferous wood, also called as crude sulphate turpentine (CST) which is predominantly composed of volatile unsaturated $C_{10}H_{16}$ terpene isomers derived from pitch. Due to the process chemicals used in kraft process, sulphur is included in the crude turpentine as a contaminant, amounting typically up to 6% by weight.

The crude turpentine can also be derived from mechanical pulping of wood, like from grinding and pressure grinding, thermomechanical pulping, or chemimechanical pulping. From these processes, turpentine can be retrieved in gaseous form, provided that the process is equipped with gas collecting means. Also from chipping of wood or saw mills turpentine can be recovered in gaseous form.

Also a mixture of various crude turpentines can be used as the terpene-based raw material in the feedstock. Further, the terpene feed can be composed of one or more terpene compounds like α-pinene which is/are isolated from a terpene mixture, such as from the crude sulphate turpentine.

Still further, sulphur-containing $C_5$ to $C_{10}$ hydrocarbon streams from wood processing industry or side streams from wood processing industry can be used as terpene-based compounds.

Also turpentine distillation bottoms can be used as terpene-based compounds in the feedstock.

Further, turpentine separated from crude tall oil which is retrieved from kraft pulping process is a suitable source of terpene-based compounds.

The term "tall oil" or "crude tall oil" refers to a byproduct of the kraft process of wood pulp manufacture. Crude tall oil contains generally both saturated and unsaturated oxygen-containing organic compounds such as rosins, unsaponifiables, sterols, rosin acids (mainly abietic acid and its isomers), fatty acids (mainly linoleic acid, oleic acid and linolenic acid), fatty alcohols, sterols and other alkyl hydrocarbon derivatives, as well as inorganic impurities discussed above (alkaline metal (Na, K) compounds, sulphur, silicon, phosphorus, calcium and iron compounds). "Tall oil" also refers to fatty acids and free fatty acids derived from tall oil and esters derived from tall oil or tall oil free fatty acids.

In an embodiment of the invention, the feedstock is substantially composed of crude tall oil (hereinafter also referred to as CTO) and crude sulphate turpentine (hereinafter also referred to as CST). CTO is mainly composed of fatty acids and resin acids with a chain length varying between $C_{12}$ and $C_{18}$, and fused ring systems as abietic acids and sitosterols. Typically, CTO also contains minor amounts of inorganic impurities like residual metals such as Na, K, Ca, Fe, sulphur compounds and other elements like phosphorus and silicon that are harmful to the activity of the catalyst. CTO can also contain some amounts of crude turpentine. The composition of the CTO varies depending on the specific wood species. CTO is especially useful to be processed to diesel range hydrocarbons.

CST is mainly composed of an oil mixture of terpenes derived from pitch. Terpenes are a wide range of volatile hydrocarbons having a chemical formula of $C_{10}H_{16}$, including typically unsaturated mono- and bicyclic hydrocarbons. The main terpene components are α-pinene, β-pinene and Δ-3-carene. The major component is typically α-pinene. CST also contains a relatively high amount of sulphur, up to 6%, as a contaminant.

The CTO and/or CST can be purified before they are subjected to the hydroprocessing treatment. Purification can be accomplished in any appropriate manner, such as by means of washing with washing liquid, filtering, distillation, degumming, depitching etc. Also, a combination of the above mentioned purification methods can be used. All these purification methods are well known in the art and are not discussed here in further detail. Purification of said raw materials may facilitate the accomplishment of the process of the invention where the content of any harmful substances, like metal ions, sulphur, phosphorus and lignin residuals in CTO, is reduced.

Said raw materials can also be utilized in an unpurified form. In an embodiment, the feedstock comprises purified CTO and unpurified CST. CST typically contains organic sulphur compounds as a contaminant but no metal ions. In the process of the invention, the organic sulphur compounds in CST are beneficially utilized for activating the hydroprocessing catalyst used in the process. CST can thus be used in an unpurified form in the invention.

In the context of the present invention, the term "hydroprocessing treatment" refers to a treatment where the feedstock is contacted with hydrogen gas under catalytic conditions where several chemical reactions occur. The main reactions in the hydroprocessing treatment include: deoxygenation of CTO by means of decarboxylation/decarbonylation and hydrogenation with the formation of water; hydrodesulphurization of CST and CTO; hydrogenation of olefinic bonds present in the fatty acids and resin acids of CTO, and of terpene compounds of CST; ring opening of terpene compounds present in CST and of fused ring systems in CTO, and in certain circumstances, cracking the side chains of the hydrocarbon chains.

The hydroprocessing treatment provides hydrocarbons including n-paraffins, aromatic hydrocarbons, non-terpenic hydrocarbons, terpenes, acyclic, monocyclic and polycyclic hydrocarbons. In the hydroprocessing step, light gaseous compounds including hydrogen sulphide, methane and ammonia are also formed. Said compounds can be easily discarded from the process and separated from each other, if desired.

The hydroprocessing treatment is accomplished by using a hydroprocessing catalyst. In an embodiment of the invention, the catalyst is a hydrodeoxygenation (HDO) catalyst. The catalyst can be any conventional HDO/HDS catalyst known in the art. It is to be noted that any catalysts conventionally used for removal of heteroatoms from the organic compounds can be used in the process of the invention. Heteroatoms are typically sulphur, oxygen and nitrogen. HDO hydrodeoxygenation catalysts are especially intended for oxygen removal but are originally used for sulphur and nitrogen removal. In a case where HDO catalyst is specifically intended for sulphur removal, the catalyst can be described as a HDS catalyst. As stated above, both hydrodesulphurization and hydrodeoxygenation reactions of CTO and CST take place in the hydroprocessing treatment and are catalyzed by means of a HDO catalyst.

The HDO catalyst can be selected from a group consisting of $NiO/MoO_3$, $CoO/MoO_3$ and a mixture of $NiO/MoO_3$ and $CoO/MoO_3$ on a support selected from $Al_2O_3$ and $Al_2O_3$—$SiO_2$, for example. In a specific embodiment of the invention, $NiO/MoO_3$ on the $Al_2O_3$ support is used.

The HDO catalyst is advantageously capable of removing undesirable sulphur compounds present in the CST and CTO, like dimethyl sulphide, dimethyl disulphide and methyl mercaptane, by converting the organic sulphur compounds to gaseous hydrogen sulphide. It is characteristic of the HDO catalyst that sulphur has to be present to maintain the catalytic activity of the catalyst. Advantageously, hydrogen disulphide needed for catalytic activity of the catalyst is thus simultaneously provided in the hydroprocessing treatment step from the sulphur compounds inherently present in CST and CTO. Gaseous hydrogen sulphide can be easily discarded from the mixture of the hydrocarbon components formed in said step.

It may be necessary to supply supplementary sulphur to the process to maintain the catalytic activity of the HDO catalyst, depending on mixture ratio of CTO and CST in the feedstock. Supplementary sulphur can be supplied in gaseous form like hydrogen sulphide, or it can be any material that produces hydrogen sulphide in the process, like organic sulphur compounds, such as dimethyl disulphide. In an embodiment of the invention, supplementary sulphur is provided by recirculating the $H_2S$-containing gas retrieved from the mixture of hydrocarbon components produced by the process of the invention. The amount of supplementary sulphur depends on the amount of sulphur in the CST. Generally, the $H_2$ feed/$H_2S$ relation must be maintained over about 0.0001. This means that an amount of sulphur is in the range of about 100 to about 200 ppm in the feedstock. Sulphur can be fed to the hydroprocessing treatment step together with the feedstock or separately.

The amount of hydrogen gas needed to hydrogenate the olefinic bonds of the unsaturated compounds in the feed stock is determined by the amount of the feedstock. A suitable amount of hydrogen can be determined by a man having ordinary skills in the art.

Hydrocarbons including n-paraffins obtained from the hydroprocessing treatment are further subjected to isomerisation where straight carbon backbones of n-paraffins are isomerised to isoparaffins. Isoparaffins have typically mono and di branches. Isomerisation provides an improvement in cold flow properties of the diesel fuel without an adverse effect on the other properties, like cetane number. Simultaneously with the isomerisation, the HI or dewaxing catalyst removes heteroatoms such as oxygen, sulphur and nitrogen.

Isomerisation of n-paraffins is accomplished in the presence of a dewaxing catalyst. Any conventional dewaxing catalyst known in the art can be used. The catalyst is hereinafter called as an isomerisation catalyst (hereinafter referred to as HI catalyst). In an embodiment of the invention, NiW on a support selected from $Al_2O_3$, zeolite, zeolite-$Al_2O_3$, and $Al_2O_3$—$SiO_2$ is used as a HI catalyst. In a specific embodiment, NiW on an $Al_2O_3$ support is used. Like the HDO catalyst, the HI catalyst needs sulphur to maintain its catalytic activity.

In addition to capability of isomerisation of n-paraffins, the dewaxing catalyst has cracking properties. Especially, cymenes formed in the hydroprocessing treatment step are converted to toluene. Toluene has an increasing effect on the octane number of gasoline fuel. Also, isomerisation of the hydrocarbons improves the cold flow properties of diesel fuel. Isomerisation performed by means of the dewaxing catalyst in the present invention has thus a beneficial influence on quality of gasoline, diesel and jet fuels.

In another embodiment of the invention, the hydroprocessing catalyst in the hydroprocessing treatment is a dewaxing catalyst. Any conventional dewaxing catalyst known in the art can be used. In an embodiment, the dewaxing catalyst is NiW on a support selected from $Al_2O_3$, zeolite, zeolite-$Al_2O_3$, and $Al_2O_3$—$SiO_2$, preferably on an $Al_2O_3$ support. The dewaxing catalyst is able to perform the same chemical reactions as the HDO catalyst, i.e. hydrogenation of olefinic bonds of the compounds, removal heteroatoms from the compounds, and opening at least one of the bicyclic rings. In addition, the catalyst cracks and isomerizes the hydrocarbons. The cracking/isomerisation is controlled by process variables, such as pressure and/or temperature and by the properties of the catalyst, for example controlling its acidity. At the same time, sulphur compounds are reduced to hydrogen sulphide. Thus, when a dewaxing catalyst is used in the hydroprocessing step, no further isomerisation may be needed.

The hydroprocessing treatment and isomerisation can be accomplished in the same reactor or in separate reactors. Further, the HDO and HI catalysts used for hydroprocessing treatment and isomerisation, respectively, can be mixed and packed in one layer in the reactor. Preferably, the two catalysts are packed in one reactor.

The pressure in the hydroprocessing treatment and isomerisation steps can vary from about 30 to about 200 bar, preferably about 30 to about 100 bar. Especially, when a HDO catalyst is used in the hydroprocessing treatment and the HDO catalyst and a HI catalyst for isomerisation are packed in separate reactors, the hydroprocessing treatment is performed at a pressure ranging from 30 to 100 bar, preferably 30 to 70 bar. If a HI catalyst used in the hydroprocessing treatment and isomerization is packed in two separate reactors, i.e. a first reactor and a second reactor, the first reactor arranged upstream of the second reactor is operated at a pressure ranging from 30 to 200 bar, preferably 30 to 100 bar, more preferably 30-70 bar. The second reactor is operated at a pressure of 30 to 200 bar, preferably 70 to 100 bar, more preferably 60 to 100 bar.

When a hydroprocessing catalyst and a dewaxing catalyst are packed in a single reactor, the pressure of the reactor can vary between 30 to 200 bar, preferably 30 to 100 bar, more preferably 30 to 70 bar.

The hydroprocessing treatment and isomerisation are carried out at a temperature in the range of about 280° C. to about 500° C., preferably at about 330° C. to about 430° C. Especially, when a HDO catalyst is used in the hydroprocessing treatment and the HDO catalyst and a HI catalyst for isomerisation are packed in separate reactors, the hydroprocessing treatment is performed at a temperature ranging from 310 to 380° C., preferably 350 to 370° C. If a HI catalyst is used in the hydroprocessing treatment and the catalyst and a HI catalyst for isomerisation are packed in separate reactors, the hydroprocessing treatment is performed at a temperature ranging from 280 to 500° C., preferably 330 to 430° C. Isomerisation is then accomplished in a separate reactor at temperature gradient ranging from 430 to 350° C.

When a hydroprocessing catalyst and a dewaxing catalyst are packed in separate layers in a single reactor, the temperature of the hydroprocessing catalyst layer can vary between 310 to 380° C., preferably 330 to 360° C. for a HDO catalyst, and between 280 to 500° C., preferably 330 to 430° C. for a dewaxing catalyst. Isomerisation in the subsequent dewaxing catalyst layer can be performed at a temperature ranging from 280 to 500° C., preferably 330 to 430° C.

The hydroprocessing steps are highly exothermic reactions in which temperature can rise to a level which is detrimental to the stability of the catalyst and/or product quality. In some cases, it may be necessary to control the temperature variations. Recirculation of at least a portion of the product stream obtained from the isomerisation step, i.e. a mixture of fuel grade hydrocarbons, provides an efficient means for constraining the exothermic reaction whereby the recycled product stream acts as a media lowering the temperature of the bed in a controlled manner. Also, only a hydrocarbon fraction obtained from isomerisation can be recycled. In an embodiment of the invention, a heavy fraction of the product stream, said fraction comprising >C17, the length of the hydrocarbon chain depending on the product produced, is circulated back to the feedstock.

The mixture of hydrocarbons obtained from the isomerisation step includes fuel grade hydrocarbons having a boiling point at most 370° C. In order to be able to utilize the obtained hydrocarbon mixture in an optimum manner, the mixture is further subjected to separation to separate the mixture into various fuel grade hydrocarbon fractions. Separation can be realized conveniently by distillation. Specifically, product streams having distillation curves conforming to those of standardized diesel, gasoline, naphtha and jet fuels are achieved. As a general, hydrocarbons distilling at a temperate range from 180° C. to 370° C. are obtained as a middle distillate conforming to diesel fuel quality standard EN 590. Hydrocarbons distilling at temperatures ranging from 150° C. to 210° C. are useful as high quality gasoline fuel. They conform to the standard EN 228. Hydrocarbons having a distillation temperature between 160° C. and 300° C. are useful as aviation applications, generally referred to as jet fuel. The jet fuel conforms to standard ASTM D-1655. The composition of the products obtained with the method of the present invention depends on the feed material used as well as on the operation conditions of the process.

The products obtained can be used as fuel as such or they can be used as fuel components and be blended with other fuels or fuel components. When the products of the present invention are blended as fuel components the properties of the final blends conform to those of the desired standards, especially to EN590, EN228 and ASTM D-1655.

In separation, also hydrocarbon fractions distilling at temperatures ranging from 40° C. to 210° C. and at a temperature of about 370° C. are obtained. These fractions are useful as high quality gasoline fuel and naphtha fuel, respectively, or as blending components for these fuels. Said hydrocarbon fractions can also be used as blending components in standard fuels.

Another object of the invention is to provide an apparatus for producing hydrocarbon components: The apparatus is adapted to realize an embodiment of the process of the invention. The apparatus comprises one or more hydroprocessing reactors 1, 1',
a feedstock inlet conduit 4 for introducing a feedstock comprising tall oil and terpene-based compounds to the one or more hydroprocessing reactors,
a hydrogen inlet conduit 6 for introducing hydrogen to the one or more hydroprocessing reactors,
a product outlet conduit 8 for recovering hydrocarbon components from the one or more hydroprocessing reactors, wherein at least one of the hydroprocessing reactors comprises a catalyst layer 3 of a dewaxing catalyst.

With reference to FIG. 1, crude tall oil is supplied to a hydroprocessing reactor 1 via feedstock inlet conduit 4. Conduit 5 for supplying crude sulphate turpentine to the reactor is combined with the feedstock inlet conduit 4 to provide a single unidirectional feedstock flow.

If desired, a purification section 15 can be arranged in connection with hydroprocessing reactor 1 for purification of CTO prior to its supply to reactor 1, as shown by the dotted line in FIG. 1. The purification section can comprise the purification of CTO with a washing liquid, for example. The purification can be accomplished batchwise or continuously.

Hydrogen is supplied via conduit 6 to reactor 1. Conduit 6 is arranged to reactor 1 at an initial end of the reactor. Hydrogen can also be fed to the reactor at one or several positions close to the one or both catalyst layers 3, 3', as shown by the dotted line 60.

A first catalyst layer 3' and a second catalyst layer 3 are packed in the reactor. The first catalyst layer 3' is arranged upstream of the second catalyst layer 3. The HDO catalyst is packed in the first catalyst layer 3', and HI catalyst is packed in the second catalyst layer 3.

Hydroprocessing treatment and isomerisation of the feedstock are accomplished in reactor 1. As a main rule, catalytic hydrodeoxygenation and hydrodesulphurization reactions, saturation of olefinic bonds and ring opening of the terpene and tall oil compounds in the feedstock take place in the catalyst layer 3. Isomerisation reactions and cracking of hydrocarbons take place pre-dominantly in the catalyst layer 3'.

Guard beds 7 comprising suitable material, such as $Al_2O_3$, SiC or glass beads can be arranged in reactor 1. Their task is to act as guard beds against harmful substances in the feed. In FIG. 1, guard beds 7 are arranged between the two catalyst layers, and upstream and downstream of catalyst layers 3 and 3', respectively. When a guard bed is arranged in reactor 1 as the first layer to receive the feedstock via inlet conduit 4, upstream of the catalyst layer 3', it also acts as a preheating layer for the feed. It also enhances the even distribution of the feed to the catalyst. An intermediate guard bed disposed between the two catalyst layers prevents the two catalyst layers to mix with each other and facilitates the operating of the first and second catalyst layers in different temperatures.

Temperatures of the catalyst layers 3' and 3 are typically about 340° C. and 380° C., respectively. Reactor 1 is operated at a pressure of 50 bar, for example.

The two catalyst layers can be diluted with an appropriate medium. The diluting material can be for example material used in the guard beds described above, or another catalyst suitable for hydrogenation. Dilution of the catalysts helps in controlling the exothermic balance of the reaction. In an embodiment, the first catalyst layer 3' comprises diluted HDO catalyst material, and the second catalyst layer 3 comprises undiluted HI catalyst material.

In an embodiment of the invention, one of the catalyst layers 3 and 3' is omitted and the HDO catalyst and the HI catalyst are mixed together and packed in one layer in reactor 1.

Supplementary sulphur can be supplied to reactor 1 via sulphur feed conduit 9. Conduit 9 can be joined to feedstock inlet conduit 4 and/or hydrogen inlet conduit 60.

CTO and CST, i.e. the feedstock, are pumped to reactor 1 at a desired speed. Feed rates WHSV (weight hourly spatial velocity) of the two raw materials are proportional to an amount of the catalyst: WHSV is calculated according to the following equation:

$$WHSV[h^{-1}] = \frac{V_{feed[g/h]}}{m_{catalyst[g]}}$$

wherein $V_{feed[g/h]}$ means a pumping velocity of the feedstock, and $m_{catalyst[g]}$ means an amount of the catalyst.

WHSV of the feedstock is typically about 0.6.

The relation $H_2$ feed/feedstock is typically in the range of 1 200 to 1 400 Nl/l.

The product stream including a mixture of hydrocarbon components from reactor 1 is recovered via product outlet conduit 8. At least a portion of the product stream can be circulated back to the reactor 1 through product recirculation conduit 80 as shown by the dotted line. In the recirculation, the product can be combined with the feedstock inlet conduit 4 into a single feed flow and supplied to reactor 1.

At least a portion of the product stream recovered via product outlet conduit 8 is further supplied to a separator 2 where one or several hydrocarbon fractions are separated. The separator is appropriately a distillation apparatus in which the hydrocarbon fractions are separated based on differences in boiling points. The various hydrocarbon fractions are recovered from the separator via fuel outlet conduit 10.

The mixture of hydrocarbon components supplied to the separator also includes a heavy fraction composing mainly of $C_{21}$ to $C_{100+}$ hydrocarbons having a boiling point of above about 370° C., such as sterolic components and polymers. The heavy fraction is discarded from the separator via conduit 11 and circulated back to hydroprocessing reactor 1. Conduit 11 can be joined to product recirculation conduit 80 as shown in FIG. 1. Conduit 11 can also be joined directly to feedstock inlet 4 (not shown).

Light gaseous compounds including $H_2$ formed in the hydroprocessing treatment can be led via conduit 12 to a hydrogen separator 13. Hydrogen is recovered and circulated via hydrogen circulation conduit 14 back to hydrogen inlet conduit 6.

Figure 2:
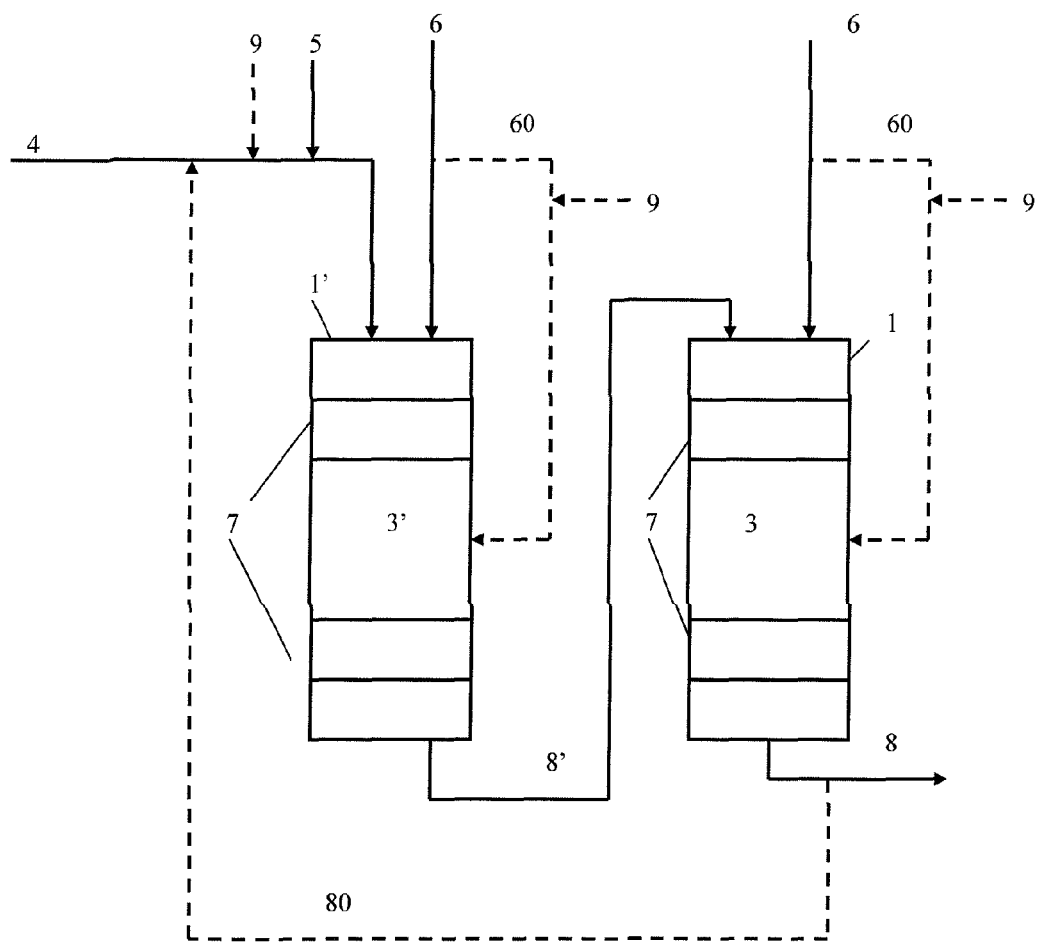
FIG. 2 shows another embodiment of the apparatus of the invention.

FIG. 2 shows an embodiment of the invention, where the hydroprocessing treatment and the isomerisation including cracking are realized in two separate reactors, i.e. in a first reactor 1' and a second reactor 1, respectively. HDO and HI catalysts are packed in two separate catalyst layers. A first catalyst layer 3' of HDO catalyst is packed in the first reactor 1', and a second catalyst layer 3 of HI catalyst is packed in the second reactor 1. The first reactor 1' is arranged upstream of the second reactor 1. In an embodiment of the invention, the first catalyst layer 3' includes diluted HDO catalyst, whereas the second catalyst layer 3 includes undiluted HI catalyst. Guard beds 7 are arranged in the first and second reactors 1' and 1.

Crude tall oil is fed to the first reactor 1' via feedstock inlet conduit 4. Conduit 5 for supplying crude sulphate turpentine to the reactor is combined with the feedstock inlet conduit 4 to provide a single unidirectional feedstock flow. A purification section 15 can be arranged in the similar manner as in FIG. 1 (not shown).

WHSV of the feedstock to reactor 1' is typically in the range of about 0.6 to about 1.2, for example about 1. Reactor 1' is typically operated at a temperature of about 360° C. and under a pressure of about 50 bar. The relation $H_2$ feed/feedstock is typically <500 Nl/l.

The product obtained from the first reactor 1' is recovered via pipe 8' and supplied to the second reactor 1 for isomerisation and cracking. The product stream including a mixture of hydrocarbon components is recovered via product outlet pipe 8 from the second reactor 1.

$H_2$ feed is supplied to both reactors 1' and 1 via hydrogen inlet conduit 6. Conduit 6 can enter reactors 1, 1' at an initial end of the reactors where the feeds via conduits 4 and 8' enter the reactors. Hydrogen can also be fed to a position of one or both of the catalyst layers in the reactor as shown by the dotted line 60.

WHSV of the feedstock to reactor 1 is typically in the range of about 0.75 to about 0.8. Reactor 1 is typically operated at a temperature gradient 410/380/360° C. and under a pressure of about 90 bar. The relation $H_2$ feed/feedstock is typically about 735 Nl/l.

The product stream including a mixture of hydrocarbon components from reactor 1 is recovered via product outlet conduit 8. At least a portion of the product stream can be circulated back to hydroprocessing reactor 1' through product recirculation conduit 80 as shown by the dotted line. In the recirculation, the product can be combined with the feedstock inlet conduit 4 into a single feed flow and supplied to reactor 1'.

Supplementary sulphur can be supplied to both reactors 1' and 1 via sulphur feed conduit 9. Conduit 9 can be joined to feedstock inlet conduit 4 and/or hydrogen inlet conduit 60.

At least a portion of the product stream recovered via product outlet conduit 8 can be further led to separator 2 in a similar manner as shown in FIG. 1 (not shown).

A conduit in this application can be any kind of pipe, tube, hose or connecting device suitable for this purpose.

It is another object of the invention to provide a use of the hydrocarbon components produced by the process of the invention as fuel or as an additive in fuel compositions.

It is a further object of the invention to provide a use of the hydrocarbon components produced by the process of the invention as fuel or as an additive in fuel compositions.

It is still a further object of the invention to provide a use of a NiW catalyst on a support selected from $Al_2O_3$, zeolite, zeolite-$Al_2O_3$, and $Al_2O_3$—$SiO_2$ for producing fuel or an additive for fuel compositions from a feedstock comprising tall oil and terpene-based compounds.

The invention claimed is:

1. A process for producing hydrocarbon components, comprising:
purifying a crude tall oil to reduce metal ions, sulphur, phosphorous and lignin residuals in the crude tall oil;
combining a crude sulphate turpentine obtained from kraft pulping of wood with the purified crude tall oil to produce a feedstock consisting of said purified crude tall oil and said crude sulphate turpentine;
hydroprocessing the feedstock in the presence of hydrogen and a $NiO/MoO_3$ catalyst on an $Al_2O_3$ support, at a temperature of about 280° C. to about 500° C. and at a pressure of about 30 bar to about 200 bar, to produce hydrocarbon components comprising n-paraffins; and
isomerizing the hydrocarbon components comprising n-paraffins in the presence of hydrogen and a NiW catalyst on a zeolite-$Al_2O_3$ support, at a temperature of about 280° C. to about 500° C. and a pressure of about 30 bar to about 200 bar, to form a mixture of hydrocarbon components.

2. The process of claim 1 wherein a portion of the mixture of hydrocarbon components obtained from the isomerisation is circulated back to the hydroprocessing treatment.

3. The process of claim 1 wherein a pumping speed WHSV of the feedstock is 0.6-1.2 $hour^{-1}$.

4. The process of claim 1 wherein the mixture of the hydrocarbon components is separated into gasoline, diesel, jet and naphtha range hydrocarbon fractions.

5. A process for producing hydrocarbon components, comprising:
purifying a crude tall oil to reduce metal ions, sulphur, phosphorous and lignin residuals in the crude tall oil;
combining the purified crude tall oil with a crude sulphate turpentine containing up to 6% by weight sulphur to produce a feedstock consisting of said purified crude tall oil and said crude sulphate turpentine;
hydroprocessing the feedstock in the presence of hydrogen and a $NiO/MoO_3$ hydroprocessing catalyst on an $Al_2O_3$ support, at a temperature of about 280° C. to about 500° C. and at a pressure of about 30 bar to about 200 bar, to convert dimethyl sulphide, dimethyl disulphide, and methylmercaptan in the feedstock to gaseous hydrogen sulphide, and to produce hydrocarbon components comprising n-paraffins;
isomerizing the hydrocarbon components comprising n-paraffins in the presence of hydrogen and a NiW catalyst on a zeolite-$Al_2O_3$ support, at a temperature of about 280° C. to about 500° C. and a pressure of about 30 bar to about 200 bar, to form a mixture of hydrocarbon components; and
circulating a portion of the mixture of hydrocarbon components obtained from the isomerisation back to the hydroprocessing treatment.

* * * * *